US008698073B2

(12) United States Patent
Li et al.

(10) Patent No.: US 8,698,073 B2
(45) Date of Patent: Apr. 15, 2014

(54) ION COLLECTING DEVICE FOR ION MOBILITY SPECTROMETER AND ION MOBILITY SPECTROMETER

(75) Inventors: Yuanjing Li, Beijing (CN); Zhiqiang Chen, Beijing (CN); Qingjun Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 73 days.

(21) Appl. No.: 12/997,751

(22) PCT Filed: Jun. 28, 2010

(86) PCT No.: PCT/CN2010/074568
§ 371 (c)(1),
(2), (4) Date: Feb. 8, 2011

(87) PCT Pub. No.: WO2011/000294
PCT Pub. Date: Jan. 6, 2011

(65) Prior Publication Data
US 2011/0168884 A1  Jul. 14, 2011

(30) Foreign Application Priority Data

Jun. 30, 2009  (CN) .......................... 2009 1 0088634

(51) Int. Cl.
*H01J 49/26* (2006.01)
(52) U.S. Cl.
USPC ............ 250/287; 250/281; 250/283; 250/489
(58) Field of Classification Search
USPC .......................... 250/281–283, 288, 489, 287
See application file for complete search history.

(56) References Cited

U.S. PATENT DOCUMENTS

| 4,839,143 | A | * | 6/1989 | Vora et al. ........................ 422/98 |
| 5,021,654 | A | * | 6/1991 | Campbell et al. ............. 250/287 |
| 5,053,343 | A | * | 10/1991 | Vora et al. ...................... 436/153 |
| 5,200,614 | A | * | 4/1993 | Jenkins .......................... 250/286 |
| 7,705,296 | B2 | * | 4/2010 | Wu ................................ 250/282 |

(Continued)

FOREIGN PATENT DOCUMENTS

| CN | 1544931 | 11/2004 |
| CN | 201141853 | 10/2008 |

OTHER PUBLICATIONS

First Office Action of related Chinese patent application No. 200910088634.6 in Chinese and brief English translation, date mailed Jun. 7, 2011, 6 pages.

(Continued)

*Primary Examiner* — David A Vanore
*Assistant Examiner* — Wyatt Stoffa
(74) *Attorney, Agent, or Firm* — Westman, Champlin & Koehler, P.A.

(57) ABSTRACT

The present invention provides an ion collection device for an ion mobility spectrometer and an ion mobility spectrometer. The ion collection device comprises: an aperture grid for restraining influence of ion drift movement in a drift region on ion collection; and a first electrode disposed at a downstream side of the aperture grid in an ion drift direction, the first electrode is mechanically and electrically coupled with the aperture grid. With the above configuration, the aperture grid and the first electrode are at the same electric potential, and form a focusing electrical field with an ion collection part. Therefore, ions entering the collection region will not scatter into a shield cover.

15 Claims, 2 Drawing Sheets

(56) References Cited

U.S. PATENT DOCUMENTS

| | | | |
|---|---|---|---|
| 7,807,964 B2* | 10/2010 | Li et al. | 250/287 |
| 7,888,635 B2* | 2/2011 | Belov et al. | 250/283 |
| 2001/0032929 A1* | 10/2001 | Fuhrer et al. | 250/281 |
| 2002/0017605 A1* | 2/2002 | Jenkins et al. | 250/287 |
| 2003/0155504 A1* | 8/2003 | Motchkine et al. | 250/287 |
| 2006/0054809 A1* | 3/2006 | Giannantonio et al. | 250/292 |
| 2007/0114395 A1* | 5/2007 | Swenson et al. | 250/292 |
| 2007/0278396 A1* | 12/2007 | Wu | 250/282 |
| 2009/0078861 A1* | 3/2009 | Hill et al. | 250/282 |
| 2009/0166530 A1* | 7/2009 | Li et al. | 250/282 |
| 2009/0189069 A1* | 7/2009 | Chen et al. | 250/282 |
| 2009/0206246 A1* | 8/2009 | Munro | 250/282 |
| 2010/0065755 A1* | 3/2010 | Li et al. | 250/424 |
| 2011/0133072 A1* | 6/2011 | Li et al. | 250/282 |

OTHER PUBLICATIONS

Office Action from German Patent Application No. 11 2010 000 008.5, dated Mar. 19, 2012, 7 pages.

Translation of Office Action from German Patent Application No. 11 2010 000 008.5, dated Mar. 19, 2012, 5 pages.

Second Office Action from German Patent Application No. 11 2010 000 008.5, dated Jun. 19, 2013, along with the English translation.

* cited by examiner

ION COLLECTING DEVICE FOR ION MOBILITY SPECTROMETER AND ION MOBILITY SPECTROMETER

CROSS-REFERENCE TO RELATED APPLICATION

This application is a Section 371 National Stage Application of International Application No. PCT/CN2010/074568, filed Jun. 28, 2010, the contents of which are hereby incorporated by reference in their entirety.

BACKGROUND OF THE INVENTION

1. Field of the Invention

The present invention relates to an ion mobility spectrometer and especially an ion collecting device thereof.

2. Description of the Related Art

Referring to FIGS. 1 and 2, an ion mobility spectrometer includes an ion collecting device 50', which includes an aperture grid 15' for restraining the influence of ion drift movement in a drift region on ion collection, a Faraday plate 17' for collecting ions, an insulation member 2 for fixing the Faraday plate 17' and a shield cover 21' connected with the insulation member 2. The ion mobility spectrometer further includes an amplifier circuit for amplifying an analog signal output from the Faraday plate 17', the amplifier circuit coupled with the Faraday plate 17' via a conductor 6 and having an analog signal ground. In addition, the ion mobility spectrometer further includes a drift electrode power source for supplying power to drift electrode. The power source has a grounded output terminal which forms a ground of the drift electrode. The shield cover 21' is coupled with the analog signal ground of the amplifier circuit through a shield layer 5 of a coaxial cable, and is coupled with the ground supplying power to the drift electrode via an electric wire 7. The ions in drift region pass through the aperture grid 15' and are collected by the Faraday plate 17', which outputs a signal through a coaxial cable consisted of a core line 5 and a shield layer 6.

For the above configuration, the ions enter the collection region, and move to the shield cover 21' under the action of an electrical field generated by the aperture grid 15' and the shield cover 21', such movement toward the shield cover 21' results in loss of ions, and decreases collection efficiency.

In the example illustrated in FIG. 1, a planar aperture grid 15' is employed, and the Faraday plate 17' is disposed at a downstream side of the aperture grid 15' in an ion drift direction. The disadvantage of such structure is that the ions will spread to the shield cover 21', and consequently the collection efficiency is adversely affected.

In the example illustrated in FIG. 2, the aperture grid 15' is of a spherical shape, accordingly the aperture grid 15' causes the ions to converge, but the manufacturing cost for a spherical aperture grid is high.

Furthermore, in the above existing technology, the high voltage ground of the drift electrode power source which supplies power to the drift electrode and the analog signal ground of the amplifier circuit are jointly grounded at the shield cover 21'. As a result, noise from the high voltage ground will couple in the amplifier circuit, i.e. the front-end circuit, and influence the performance of the ion mobility spectrometer.

SUMMARY OF THE INVENTION

In order to at least partially alleviate the above-mentioned shortcoming of prior art, it is an object of the present invention to provide an ion collection device for an ion mobility spectrometer and an ion mobility spectrometer. The ion collection device and the ion mobility spectrometer may effectively collect the ions with a simple configuration.

In accordance with an aspect of the present invention, there is provided an ion collection device for an ion mobility spectrometer. The ion collection device comprises: an aperture grid for restraining influence of ion drift movement in a drift region on ion collection; and a first electrode disposed at a downstream side of the aperture grid in an ion drift direction. The first electrode is mechanically and electrically coupled with the aperture grid.

According to a further aspect of the present invention, the ion collection device may further comprise an ion collection member for collecting ions, the ion collection member including an ion collection part, wherein a space is formed inside the first electrode, and the ion collection part of the ion collection member is disposed in the space formed inside the first electrode.

According to a further aspect of the present invention, the ion collection device further comprises: a second electrode disposed at a downstream side of the first electrode in the ion drift direction, and the second electrode constitutes a grounded electrode of drift electrodes which drift ions in the ion mobility spectrometer.

According to a further aspect of the present invention, the ion collection device further comprises: a first insulation member disposed between the first electrode and the second electrode, the ion collection member connecting with the first insulation member.

According to a further aspect of the present invention, the ion collection device further comprises: a shield cover disposed at a downstream side of the second electrode in the ion drift direction, and the shield cover is separated apart from the second electrode.

According to a further aspect of the present invention, the aperture grid has a substantially flat shape.

According to a further aspect of the present invention, the first electrode has a substantially annular shape.

According to a further aspect of the present invention, the second electrode has a substantially annular shape.

According to a further aspect of the present invention, the ion collection device further comprises: a second insulation member disposed at a downstream side of the second electrode in the ion drift direction, and the shield cover is separated apart from the second electrode by the second insulation member.

According to a further aspect of the present invention, the ion collection member further comprises a signal output part coupled with the ion collection part, and the shield cover is adapted to connect with a first conductive layer of a coaxial cable which is provided at an outside of a core line of the coaxial cable, and the core line of the coaxial cable is coupled with the signal output part of the ion collection member to output a signal from the signal output part.

According to a further aspect of the present invention, the first electrode and the second electrode are substantially coaxially arranged.

According to a further aspect of the present invention, the first insulation member substantially has a shape of a plate or disk.

According to a further aspect of the present invention, the first insulation member has a centre through hole in its central part, the signal output part of the ion collection member extends through the centre through hole, and the first insulation member further comprises a plurality of through holes around the centre hole.

According to a further aspect of the present invention, an ion mobility spectrometer is provided. The ion mobility spectrometer comprises: an ion collection region part for collecting ions; and an ion collection device disposed in the ion collection region part, wherein the ion collection device comprises: an ion collection member for collecting ions, the ion collection member including an ion collection part; an aperture grid for restraining influence of ion drift movement in a drift region on ion collection; a first electrode disposed at a downstream side of the aperture grid in an ion drift direction, the first electrode being mechanically and electrically coupled with the aperture grid, wherein a space is formed inside the first electrode, the ion collection part of the ion collection member is disposed in the space formed inside the first electrode; and a first insulation member disposed at a downstream side of the first electrode in the ion drift direction, the ion collection member connecting with the first insulation member.

According to a further aspect of the present invention, the ion mobility spectrometer further comprises a second electrode disposed at a downstream side of the first insulation member in the ion drift direction, and the second electrode constitutes a grounded electrode of drift electrodes which drift the ions in the ion mobility spectrometer.

According to a further aspect of the present invention, the ion mobility spectrometer further comprises a shield cover disposed at a downstream side of the second electrode in the ion drift direction, and the shield cover is separated apart from the second electrode.

According to a further aspect of the present invention, the aperture grid has a substantially flat shape.

According to a further aspect of the present invention, the first electrode has a substantially annular shape.

According to a further aspect of the present invention, the ion collection member further comprises a signal output part coupled with the ion collection part.

According to a further aspect of the present invention, the shield cover connects with a first conductive layer of a coaxial cable which is provided at an outside of a core line of the coaxial cable, and the core line of the coaxial cable is coupled with the signal output part of the ion collection member to output a signal from the signal output part.

According to a further aspect of the present invention, the ion mobility spectrometer further comprises: an amplifier circuit, an input of the amplifier circuit receives the signal output from the signal output part through the core line of the coaxial cable, and the shield cover is coupled with an analog ground of the amplifier circuit through the first conductive layer of the coaxial cable.

According to a further aspect of the present invention, the second electrode is coupled with the analog ground of the amplifier circuit at a side of an output of the amplifier circuit.

According to a further aspect of the present invention, the ion mobility spectrometer further comprises: an amplifier circuit shield casing for shielding the amplifier circuit; and a conductive casing of the ion collection region part, wherein the coaxial cable comprises a second conductive layer disposed at outside of the first conductive layer, the second conductive layer is coupled with the amplifier circuit shield casing and the conductive casing of the ion collection region part.

According to a further aspect of the present invention, the ion mobility spectrometer further comprises: a drift electrode power source for supplying power to the drift electrodes, the drift electrode power source has a drift electrode power source shield casing, and the drift electrode power source has a grounded output terminal which is coupled with the second electrode and is coupled with the analog ground of the amplifier circuit at the side of the output of the amplifier circuit.

Some embodiments of the ion collection device according to present invention effectively improve collection of ions, facilitate output of the signal, and improve signal-to-noise ratio.

DETAILED DESCRIPTION OF THE EMBODIMENTS

A further description of the invention will be made as below with reference to embodiments of the invention taken in conjunction with the accompanying drawings.

Figure 1:
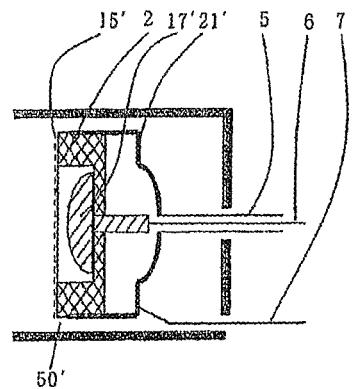
FIG. 1 is a schematic view of an ion collection device of a prior art ion mobility spectrometer.
Figure 2:
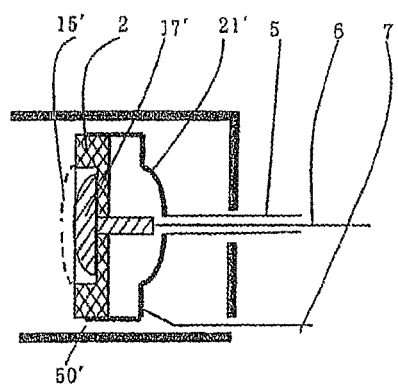
FIG. 2 is a schematic view of an ion collection device of another prior art ion mobility spectrometer.
Figure 3:
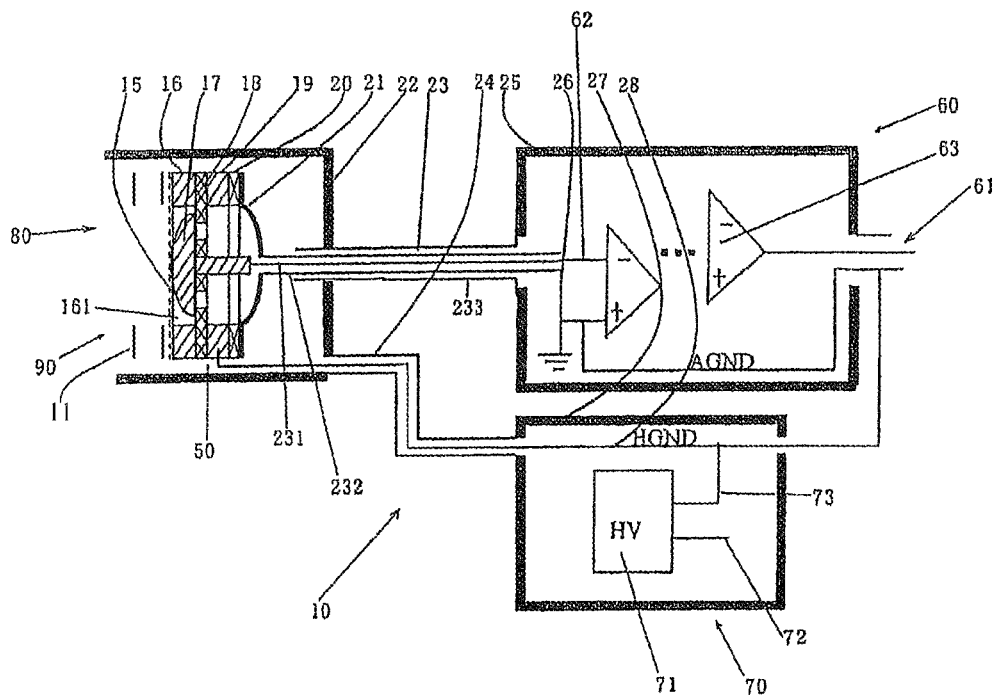
FIG. 3 is a schematic view of an ion collection device of an ion mobility spectrometer according to an embodiment of the present invention.

As illustrated in FIG. 3, in some embodiments of the present invention, an ion mobility spectrometer according to an embodiment of the present invention comprise: an ion collection region part 90 for collecting ions; and an ion collection device 50 provided in the ion collection region part 90.

Referring to FIG. 3, the ion mobility spectrometer 10 according to an embodiment of the present invention may further comprise: an amplifier circuit part 60, and a drift electrode power source 70 for supplying power to drift electrodes 11

As illustrated in FIG. 3, the ion collection device 50 of the ion mobility spectrometer according to an embodiment of the present invention comprises: an aperture grid 15 for restraining the influence of ion drift movement in a drift region on ion collection; and a first electrode 16 which is disposed at a downstream side (i.e., a right side in FIG. 3) of the aperture grid (or restraining grid) 15 in an ion drift direction 80. The first electrode 16 is mechanically and electrically coupled with the aperture grid 15.

In some embodiments of the present invention, as illustrated in FIGS. 3, 6, 7, 8, 9, the ion collection device 50 of the ion mobility spectrometer further comprises an ion collection member 17 for collecting ions, the ion collection member 17 including an ion collection part 171. A space 161 is formed inside the first electrode 16, and the ion collection part 171 of the ion collection member 17 is provided in the space 161 formed inside the first electrode 16.

In some other embodiments of the present invention, the ion collection part 171 of the ion collection member 17 is located at an outside of the space 161 formed inside the first electrode 16 instead of being disposed in the space 161 formed inside the first electrode 16. For instance, the ion collection part 171 of the ion collection member 17 is located adjacent to the first electrode 16 or spaced away from the first electrode 16.

In some embodiments of the present invention, as illustrated in FIGS. 3, 6, 7, 8, 9, the ion collection device 50 of the ion mobility spectrometer further comprises a first insulation member 18 disposed at a downstream side of the first electrode 16 in the ion drift direction 80, and the first insulation member 18 is connected to the ion collection member 17.

In some other embodiments of the present invention, the ion collection member 17 of the ion collection device 50 of the ion mobility spectrometer may be fixed to other components or insulation members in a collection region of the ion mobility spectrometer. Alternatively, the ion collection member 17 of the ion collection device 50 may be fixed to any well-known, appropriate components of the ion mobility spectrometer. The ion collection member 17 may be shaped in any appropriate forms.

According to some embodiments of the present invention, as illustrated in FIG. 3, the ion collection device 50 of the ion mobility spectrometer may further comprise: a second electrode 19 disposed at a downstream side of the first insulation member 18 in the ion drift direction 80. The second electrode 19 constitutes a grounded electrode of drift electrodes which drift the ions in the ion mobility spectrometer. In other words, the second electrode 19 as a high voltage ground HGND is coupled with a ground of a sequent high voltage circuit.

Figures 14, 15, 16, 17:
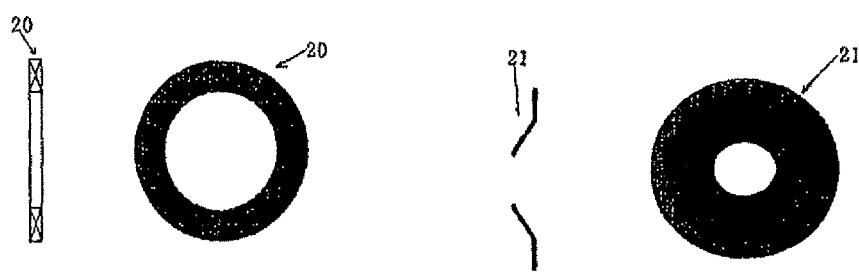
FIG. 14 is a schematic sectional view of a second insulation member of the ion collection device of the ion mobility spectrometer according to an embodiment of the present invention.
FIG. 15 is a schematic front view of the second insulation member of the ion collection device of the ion mobility spectrometer according to an embodiment of the present invention.
FIG. 16 is a schematic sectional view of a shield cover of the ion collection device of the ion mobility spectrometer according to an embodiment of the present invention.
FIG. 17 is a schematic front view of the shield cover of the ion collection device of the ion mobility spectrometer according to an embodiment of the present invention.

According to some embodiments of the present invention, as illustrated in FIG. 3, the ion collection device 50 of the ion mobility spectrometer may further comprise: a shield cover 21 disposed at a downstream side of the second electrode 19 in the ion drift direction, and the shield cover 21 is separated from the second electrode 19. An example of the shield cover 21 is shown in FIGS. 16-17.

In some embodiments of the present invention, as illustrated in FIG. 3, the shield cover 21, as an analog signal ground AGND, is coupled with an analog ground of a sequent circuit, and the high voltage ground is coupled with the analog ground at a single point at the analog ground which is at an output side of an amplifier.

According to some embodiments of the present invention, the ion collection device 50 of the ion mobility spectrometer may not include a second electrode 19. In that circumstance, for instance, in the ion collection device 50 the shield cover 21 may be directly connected on the first insulation member 18.

Figures 4, 5, 6, 7, 8, 9:
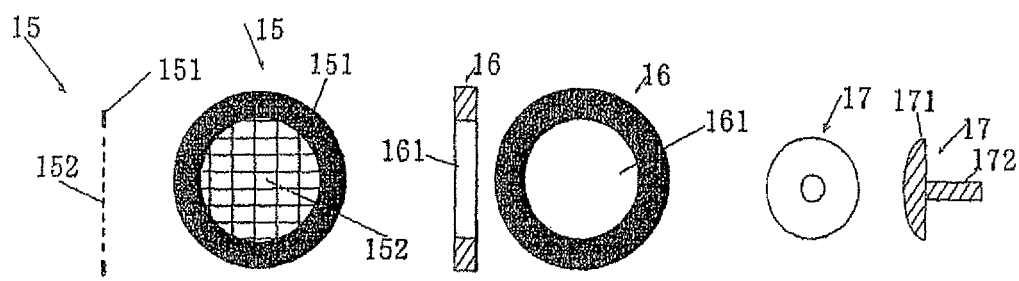
FIG. 4 is a schematic sectional view of an aperture grid of the ion collection device of the ion mobility spectrometer according to an embodiment of the present invention.
FIG. 5 is a schematic front view of the aperture grid of the ion collection device of the ion mobility spectrometer according to an embodiment of the present invention.
FIG. 6 is a schematic sectional view of a first electrode of the ion collection device of the ion mobility spectrometer according to an embodiment of the present invention.
FIG. 7 is a schematic front view of the first electrode of the ion collection device of the ion mobility spectrometer according to an embodiment of the present invention.
FIG. 8 is a schematic front view of an ion collection member of the ion collection device of the ion mobility spectrometer according to an embodiment of the present invention.
FIG. 9 is a schematic sectional view of the ion collection member of the ion collection device of the ion mobility spectrometer according to an embodiment of the present invention.

According to some embodiments of the present invention, as illustrated in FIGS. 4, 5, the aperture grid 15 may have a substantially flat shape or a shape of a flat plate. In an embodiment, referring to FIGS. 4, 5, the aperture grid 15 may comprise a conductive annular member 151 and a conductive mesh 152 which is electrically and mechanically coupled with the conductive annular member 151. Alternatively, the aperture grid 15 may be constituted by only the conductive mesh.

According to some embodiments of the present invention, as illustrated in FIGS. 6, 7, the first electrode 16 may have a substantially annular shape. Furthermore, the substantially annular first electrode 16 may have any appropriate inner surface such as a substantially tapered inner surface, a substantially cylindrical inner surface, and a substantially paraboloidal inner surface. FIGS. 6 and 7 illustrate a substantially cylindrical inner surface or a substantially cylindrical inner space 161.

Figures 10, 11, 12, 13:
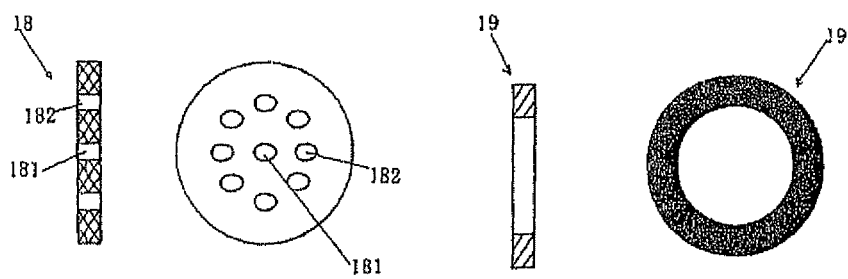
FIG. 10 is a schematic sectional view of a first insulation member of the ion collection device of the ion mobility spectrometer according to an embodiment of the present invention.
FIG. 11 is a schematic front view of the first insulation member of the ion collection device of the ion mobility spectrometer according to an embodiment of the present invention.
FIG. 12 is a schematic sectional view of a second electrode of the ion collection device of the ion mobility spectrometer according to an embodiment of the present invention.
FIG. 13 is a schematic front view of the second electrode of, the ion collection device of the ion mobility spectrometer according to an embodiment of the present invention.

According to some embodiments of the present invention, as illustrated in FIGS. 12, 13, the second electrode 19 may have a substantially annular shape. In addition, the substantially annular second electrode 19 may have any appropriate inner surface such as a substantially tapered inner surface, a substantially cylindrical inner surface, and a substantially paraboloidal inner surface. The second electrode 19 may be in the shape of a disk with a through hole, and the through hole allows a signal line to pass and to be coupled with the ion collection member 17. FIGS. 12, 13 illustrate a substantially cylindrical inner surface. Also, the second electrode 19 may be any appropriate, well-known drift electrode which drifts ions in an ion mobility spectrometer.

According to some embodiments of the present invention, as illustrated in FIG. 3, the ion collection device 50 of the ion mobility spectrometer may further comprise: a second insulation member 20 disposed at a downstream side of the second electrode 19 in the ion drift direction 80, and the second electrode 19 is separated from the shield cover 21 by the second insulation member 20.

The second insulation member 20 may have a shape of a ring as illustrated in FIGS. 14, 15, or a sheet or any other appropriate shape. The shield cover 21 may be separated from the second electrode 19 by an appropriate space, or by means of an insulation layer formed on the shield cover 21 or the second electrode 19. Also, the shield cover 21 may be separated from the second electrode 19 by any appropriate manners known to the art. For instance, a thickness of the second insulation member may be less than 0.5 mm.

According to some embodiments of the present invention, as illustrated in FIGS. 3, 8, 9, the ion collection member 17 further comprises a signal output part 172 coupled with the ion collection part 171; while the shield cover 21 is adapted to be coupled with a first conductive layer 232 of a coaxial cable 23 which is located at an outside of a core line 231 of the coaxial cable 23, and the core line 231 of the coaxial cable 23 is coupled with the signal output part 172 of the ion collection member 17 for outputting a signal from the signal output part 172.

According to some embodiments of the present invention, as illustrated in FIG. 3, the first electrode 16 and the second electrode 19 may be substantially coaxially arranged. Alternatively, the first electrode 16 and the second electrode 19 may be arranged in any other appropriate manner. For instance, the first electrode 16 and the second electrode 19 may not be coaxially arranged.

According to some embodiments of the present invention, as illustrated in FIGS. 10, 11, the first insulation member 18 may have a plurality of through holes. Alternatively, referring to FIGS. 10 and 11, the first insulation member 18 has a centre through hole 181 at its central part, and the signal output part 172 of the ion collection member 17 extends through the centre through hole 181. The first insulation member 18 further comprises a plurality of through holes 182 around the centre through hole 181.

According to some embodiments of the present invention, as illustrated in FIG. 3, an amplifier circuit part 60 comprises an amplifier circuit 63. An input 62 of the amplifier circuit 63 receives the signal output from the signal output part 172 via the core line 231 of the coaxial cable 23, and the shield cover 21 is coupled with the analog ground 26 of the amplifier circuit 63 through the first conductive layer 232 of the coaxial cable 23.

In some embodiments of the present invention, as illustrated in FIG. 3, the second electrode 19 is coupled with the analog ground 26 of the amplifier circuit 63 at a side of an output 61 of the amplifier circuit 63.

In some embodiments of the present invention, as illustrated in FIG. 3, the ion mobility spectrometer further comprises: an amplifier circuit shield casing 25 for shielding the amplifier circuit, and a conductive casing 22 of the ion collection region part 90. The coaxial cable 23 comprises a second conductive layer 232 which is disposed at outside of the first conductive layer 231, and the second conductive layer 232 is coupled with the amplifier circuit shield casing 25 and the conductive casing 22 of the ion collection region part.

In some embodiments of the present invention, as illustrated in FIG. 3, the drift electrode power source 70 has a grounded output terminal 73 and a high voltage output terminal 72. The grounded output terminal 73 is coupled with the second electrode 19 via a conductor 28, and is coupled to the analog ground 26 of the amplifier circuit 63 at the side of the output 61 of the amplifier circuit 63. Referring to FIG. 3, the drift electrode power source 70 further comprises a drift electrode power source shield casing 27, and this shield casing 27 is coupled with the casing 22 of the ion collection region part 90 via a conductor 24. The conductor 24 and the conductor 28 constitute a coaxial cable. The coaxial cable 23 is a tri-coaxial cable, as illustrated in FIG. 3.

In some embodiments of the present invention, insulation and sheath material of the tri-coaxial cable is polytetrafluoroethylene.

With such configuration, the aperture grid 15 and the first electrode 16 are at the same electric potential, and form a focusing electrical field with the Faraday plate which serves as ion collection member 17, whereby the ions entering the collection region will not scatter to the shield cover 21, and hence the collection efficiency (or ratio) is enhanced Moreover, in some embodiments of the present invention, the second electrode 19 and the shield cover 21 are electrically separated from each other, and therefore the high voltage ground and the analog signal ground are separated from each other at the most sensitive input of the amplifier circuit, and are coupled with each other at the analog ground where the signal has been amplified, and hence noise of the high voltage ground has less influence on the signal amplification.

In addition, because the aperture grid 15 and the first electrode 16 may constitute a focusing structure, an area of the Faraday plate (serving as the ion is collection member 17 that faces the drift of the ions may be smaller.

In some embodiments of the present invention, the second insulation member 20 is porous, the second electrode 19 is provided, and the Faraday plate serving as the ion collection member 17 are located far away from the shield cover 21, whereby capacitance between the Faraday plate and the shield cover 21 is effectively reduced, and junction capacitance noise at the input of the circuit is decreased.

Furthermore, in some embodiments of the present invention, the second electrode 19 and the shield cover 21 are at the same electric potential, and thus the SNR is improved without sacrificing shielding capability of the shield cover 21.

The invention claimed is:

1. An ion collection device for an ion mobility spectrometer having drift electrodes which drift ions in the ion mobility spectrometer and a drift electrode power source for supplying power to the drift electrodes, the ion collection device comprising:
    an aperture grid for restraining influence of ion drift movement in a drift region on ion collection;
    a first electrode disposed at a downstream side of the aperture grid in an ion drift direction, the first electrode being mechanically and electrically coupled with the aperture grid;
    a second electrode disposed at a downstream side of the first electrode in the ion drift direction,
    a shield cover disposed at a downstream side of the second electrode in the ion drift direction, the shield cover being separated apart from the second electrode, wherein the drift electrode power source has a grounded output terminal which is coupled with the second electrode,
    an ion collection member for collecting ions, said ion collection member including an ion collection part, wherein a space is formed inside the first electrode, and the ion collection part of the ion collection member is disposed in the space formed inside the first electrode, and
    a first insulation member disposed between the first electrode and the second electrode, the ion collection member connecting with the first insulation member.

2. The ion collection device of claim 1, wherein the aperture grid has a substantially flat shape.

3. The ion collection device of claim 2, wherein the first electrode has a substantially annular shape.

4. The ion collection device of claim 3, wherein the second electrode has a substantially annular shape.

5. The ion collection device of claim 4, further comprising:
    a second insulation member disposed at a downstream side of the second electrode in the ion drift direction, the shield cover being separated apart from the second electrode by the second insulation member.

6. The ion collection device of claim 4, wherein
    the ion collection member further comprises a signal output part coupled with the ion collection part, and
    wherein the shield cover is adapted to be coupled with a first conductive layer of a coaxial cable which is provided at outside of a core line of the coaxial cable, and the core line of the coaxial cable is coupled with the signal output part of the ion collection member to output a signal from a signal output part.

7. The ion collection device of claim 4, wherein the first electrode and the second electrode are substantially coaxially arranged.

8. The ion collection device of claim 6, wherein the first insulation member has substantially a shape of a plate or disk.

9. The ion collection device of claim 8, wherein the first insulation member has a plurality of through holes.

10. An ion mobility spectrometer, comprising:
an ion collection region part for collecting ions; and
the ion collection device of claim 1 disposed in the ion collection region part.

11. The ion mobility spectrometer of claim 10,
wherein the ion collection member further comprises a signal output part coupled with the ion collection part, and
wherein the shield cover is adapted to be coupled with a first conductive layer of a coaxial cable which is provided at outside of a core line of the coaxial cable, and the core line of the coaxial cable is coupled with the signal output part of the ion collection member to output a signal from the signal output part.

12. The ion mobility spectrometer of claim 11, further comprising:
an amplifier circuit, an input of the amplifier circuit receives the signal output from the signal output part through the core line of the coaxial cable, the shield cover being coupled with an analog ground of the amplifier circuit through the first conductive layer of the coaxial cable.

13. The ion mobility spectrometer of claim 12, wherein
the second electrode is coupled with the analog ground of the amplifier circuit at a side of an output of the amplifier circuit.

14. The ion mobility spectrometer of claim 13, further comprising:
an amplifier circuit shield casing for shielding the amplifier circuit; and
a conductive casing of the ion collection region part,
wherein the coaxial cable comprises a second conductive layer disposed at an outside of the first conductive layer, and the second conductive layer is coupled with the amplifier circuit shield casing and the conductive casing of the ion collection region part.

15. The ion mobility spectrometer of claim 14, wherein
the grounded output terminal is coupled with the analog ground of the amplifier circuit at the side of the output of the amplifier circuit.

\* \* \* \* \*